United States Patent [19]
Hickey, deceased et al.

[11] 4,073,179
[45] Feb. 14, 1978

[54] CLIP REMOVING DEVICE

[75] Inventors: Robert J. Hickey, deceased, late of Halifax, Mass.; by Lisa M. Hickey, administratrix, Manomet, Mass.

[73] Assignee: Codman & Shurtleff, Inc., Randolph, Mass.

[21] Appl. No.: 691,271

[22] Filed: June 1, 1976

[51] Int. Cl.² .............................................. B21D 7/00
[52] U.S. Cl. ................................ 72/409; 81/5.1 R; 81/426; 128/325; 128/334 R
[58] Field of Search ................. 72/409, 410; 81/5.1 R, 81/426; 128/325, 334 R; 29/268

[56] References Cited

U.S. PATENT DOCUMENTS

| 1,454,475 | 5/1923 | Hughes | 29/268 |
|---|---|---|---|
| 3,254,649 | 6/1966 | Wood | 81/5.1 R |
| 3,283,557 | 11/1966 | Wood | 128/334 R |
| 3,344,649 | 10/1967 | Wood | 72/409 |

*Primary Examiner*—Charlie T. Moon
*Assistant Examiner*—Gene P. Crosby
*Attorney, Agent, or Firm*—James R. Hulen

[57] ABSTRACT

A device is disclosed for removing a clip member having arms foldable about a midsection into clamping engagement about opposite sides of a tubular member. The device has a pair of jaws pivotally mounted for movement toward and away from one another. One jaw has an anvil on the tip thereof facing the other jaw and a shoulder is provided on the anvil to act as a stop for the midsection of the clip member. The other jaw has a clip deforming element facing the anvil and when the jaws are moved toward one another the element contacts the anvil at a location spaced from the shoulder. To remove a clip, the clip midsection is positioned on the anvil against the shoulder and the clip deforming element is moved toward the anvil with the clip midsection therebetween. The clip arms are thereby opened by the resultant deformation that occurs in the area of the midsection facing the tubular member.

4 Claims, 10 Drawing Figures

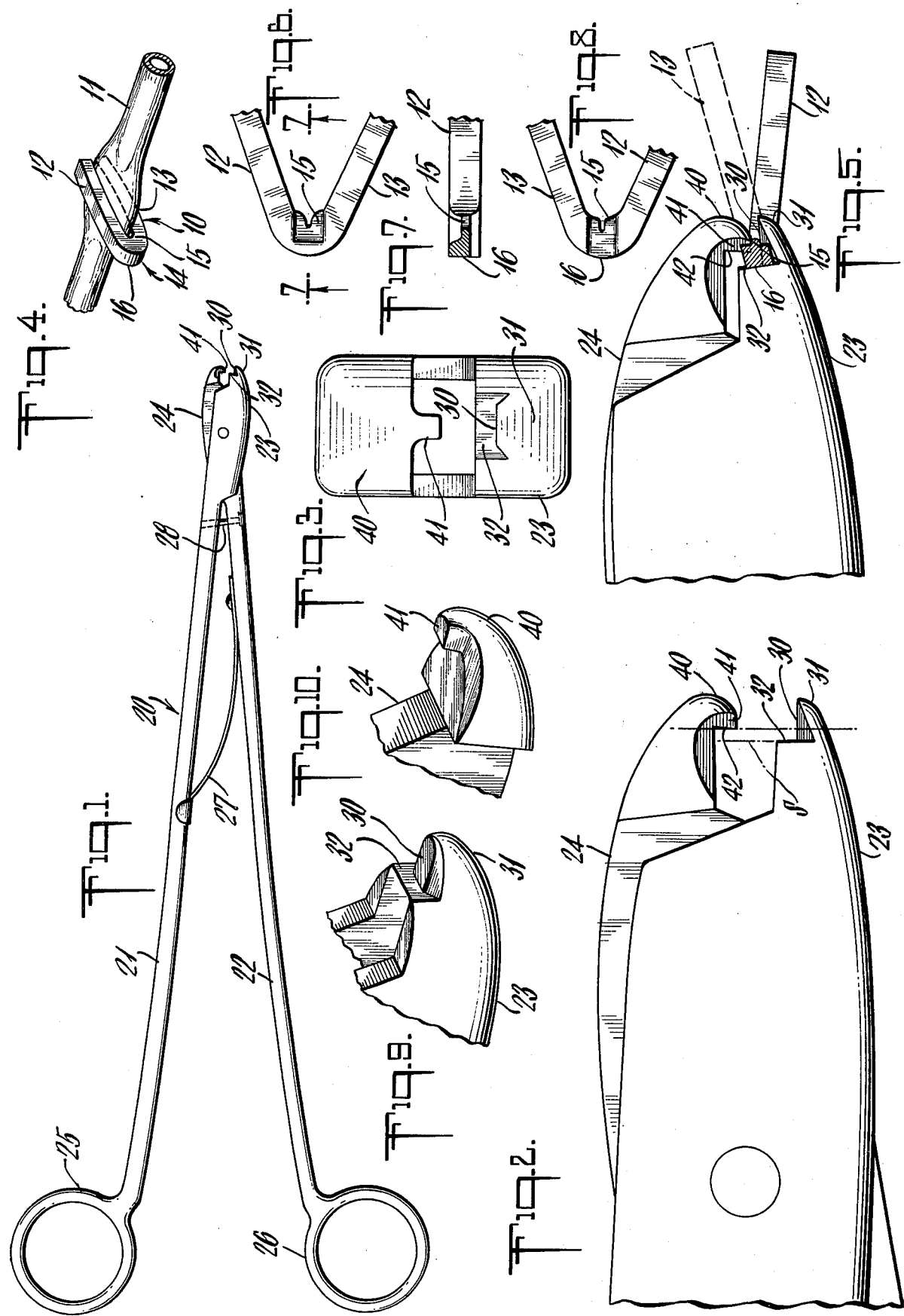

CLIP REMOVING DEVICE

BACKGROUND OF THE INVENTION

This invention relates to devices and methods for removing clip members from tubular objects and, more particularly, the invention relates to devices and methods for removing hemostatic clips from occluding position about blood vessels and the like.

To illustrate the general type of clip member, or hemostatic clip, to which the subject invention relates, reference is made to U.S. Pat. No. 3,713,533. This patent thoroughly illustrates and describes the hemostatic clip and clip applier which may be utilized to position the clip over a tubular object or blood vessel as illustrated specifically in FIG. 14 of the patent. It has been found to be very desirable to utilize this type of clip during surgery in order to expedite the surgery and to occlude minor blood vessels and other tubular vessels.

In many instances it is desirable to remove the clips prior to performing the final closing operation of the surgical procedure. Prior clip removers have been suggested for this purpose and one such remover is illustrated and described in U.S. Pat. No. 3,344,649.

Although prior devices have been suggested for the removal of hemostatic clips of the type contemplated by this invention, these prior devices failed to provide a satisfactory procedure for the removal of clips without causing undue trauma to the blood vessel and without providing the safe, efficient removal of clips that is desired by the surgeon.

SUMMARY OF THE INVENTION

The present invention provides a device for removing a clip member having arms folded about a midsection and being in occluding position over a tubular member. The device essentially comprises a pair of jaws mounted for pivotal movement toward and away from one another. One of the jaws has an anvil positioned thereon facing the other jaw and a shoulder extending inwardly toward the other jaw from the face of the anvil. The purpose for the shoulder is to accurately position the outer portion of the midsection of the folded clip so that the device will not and cannot contact the tubular object in such a manner as to cause trauma to the member. The other of the pair of jaws has an inwardly extending clip deforming element which coacts with the anvil, with the inner portion of the clip midsection therebetween, to deform that section of the clip to cause said folded arms to open. The clip deforming element, when the jaws are in the closed position, contacts the anvil at a location spaced outwardly from the shoulder. This location of the clip deforming element insures that the element will not contact the outermost portion of the clip midsection that is in contact with the shoulder. Therefore, the clip removal device will always be accurately positioned relative to the clip member and the clip deforming element and anvil will always be accurately positioned.

This invention also contemplates a new and unique method for the removal of clips from about a tubular member. This method is accomplished in a unique manner by deforming the midsection of the clip in only the inner area of the midsection that faces the tubular member. By performing this manipulative procedure, the folded arms of the clip will be forced to open and to thereby release the clip from about the tubular member.

DESCRIPTION OF THE DRAWINGS

The invention will be particularly described with reference to the following detailed description of the preferred embodiment of the invention when considered together with the attached drawings in which:

FIG. 1 is a plan view of the hemostatic clip remover embodying the features of this invention;

FIG. 2 is an enlarged fragmentary view of the pivotally mounted jaws of the device illustrated in FIG. 1;

FIG. 3 is an end view of the jaw section illustrated in FIG. 2;

FIG. 4 is a perspective view illustrating a hemostatic clip in position over a blood vessel or other fluid conduit;

FIG. 5 is a fragmentary view illustrating the jaws of the hemostatic clip remover in position over a clip member;

FIG. 6 is a fragmentary top plan view of a clip member illustrating the deformation caused by the clip remover;

FIG. 7 is a cross sectional view taken along line 7—7 of FIG. 6;

FIG. 8 is a fragmentary bottom plan view of the clip illustrated in FIG. 6 further illustrating the deformation resulting from the removal of the clip;

FIG. 9 is an enlarged fragmentary view illustrating one of the jaws of the clip remover of FIG. 1;

FIG. 10 is an enlarged fragmentary view illustrating in detail the other jaw of the clip remover of FIG. 1.

Referring first to FIG. 4, a hemostatic clip 10 is shown in occluding position about a blood vessel or other tubular member 11. Clip 10 comprises a pair of folded arms 12 and 13 which are folded about a midsection 14. Midsection 14 has an inner area 15 which is adjacent vessel 11 and an outer area 16 which is located at the outermost portion of the fold of the midsection. The manner of applying clip 10 to a vessel, as stated above, is thoroughly illustrated and described in U.S. Pat. No. 3,713,533.

Referring now to FIG. 1, the hemostatic clip remover of the present invention is shown generally at 20. Clip remover 20 preferably has a pair of pivotally connected arms 21 and 22 which terminate in jaws 23 and 24, respectively. The operating end of arms 21 and 22 have conventional ring-type gripping members 25 and 26, respectively, and the jaws are held in a predetermined spaced position by a leaf spring 27 and a stop means 28 located between the arms. This arrangement insures that jaws 23 and 24 will be in a properly spaced position for clip removal as described below. Clip remover 20 is preferably manufactured from an appropriate stainless steel material but may also be made of other suitable surgical instrument material, such as titanium.

As best illustrated in FIGS. 2, 3, 9 and 10, the clip removal structure of clip remover 20 is located at the tip of jaws 23 and 24. Referring specifically to FIG. 9, the tip of jaws 23 has an anvil 30 formed thereon which generally faces in an inward direction toward jaw 24. The extreme tip 31 of jaw 23 is smooth and rounded in order to prevent trauma to a blood vessel when a clip is being removed therefrom. Positioned rearwardly from tip 31 on anvil 30 is a shoulder 32 which acts as a stop for outer area 16 of midsection 14 when anvil 30 is brought into contact with clip 10.

Referring to FIG. 10, the tip of jaw 24 is illustrated in detail and extreme tip 40 is also relatively smooth and rounded similar to tip 31. Extending inwardly from tip 40 in a direction facing anvil 30 is a clip deforming element 41. Element 41 is located in such a position that it will contact anvil 30 at a location spaced outwardly from shoulder 32 when jaws 23 and 24 are moved together. This is best illustrated in FIGS. 2 and 5, wherein a space S is shown between the inner face 42 of element 41 and shoulder 32 which extends upwardly from anvil 30. This spacing insures that element 41 will contact inner area 15 on midsection 14 of clip 10 in the proper location for removal of the clip as hereinafter described. Although the width of space S is not critical, it is desirable that element 41 be spaced a sufficient distance from shoulder 32 so that the deformation of clip 10 will occur solely in inner area 15 of the midsection which faces vessel 11. Thus, there should be a sufficient land area between outer area 16 and inner area 15 to permit deformation in only area 15.

The method of utilizing clip remover 20 and the method of removing hemostatic clips from about tubular members will now be described in detail.

When it is desired to remove a clip, such as clip 10, from about a tubular member 11, the operator merely positions anvil 30 into contact with the side of the clip with outer area 16 firmly contacting shoulder 32. The operator may then squeeze rings 25 and 26 together and clip deforming element 41 will come into contact with the other side of inner area 15. Continues squeezing of the rings will cause area 15 to deform as illustrated best in FIGS. 6 through 8 to thereby cause arms 12 and 13 to separate. Not only will the arms separate, but the clip will be firmly gripped between anvil 30 and element 41 so that the clip may be safely removed from the wound site for disposal. Disposal of the clip may be easily accomplished by merely opening rings 25 and 26 and the instrument will thereafter be in a position for subsequent use.

It will be apparent from the foregoing that the subject invention provides a unique hemostatic clip remover which may be used to safely and efficiently remove clips from a blood vessel or other fluid conduit. The construction of the jaws of the clip remover are smooth and rounded and, therefore, minimum trauma is caused to the vessel during the clip removal procedure. Also, the structure of the anvil and clip deforming element is such that it is virtually impossible to incorrectly apply the clip remover to the clip. Furthermore, the removed clip is firmly held between anvil 30 and clip deforming element 41 during the removal operation so that the possibility of dropping the clip is greatly reduced.

What is claimed is:

1. For use with a clip member having arms foldable about a midsection into clamping engagement about opposite sides of a tubular member for strangulation when in use, a device for removing said clip member from position of use, comprising: a pair of jaws rockable about a pivot in a direction toward and away from each other between closed and open positions, respectively; an anvil formed on the tip of one of said jaws and facing inwardly toward the other of said jaws; a shoulder on said anvil spaced from the outer tip thereof forming a stop for said clip member; and a clip deforming element on the tip of said other jaw facing said anvil, said element when said jaws are closed contacting said anvil at a location spaced outwardly from said shoulder.

2. The device of claim 1, wherein the extreme tips of said jaws are rounded and smooth.

3. The device of claim 1, wherein said shoulder forms a stop for the outer area of said clip midsection, and said clip deforming element coacts with said anvil to deform the inner area of said clip midsection.

4. The device of claim 3, wherein the coaction between said element and said anvil deforms only the inner area of said clip midsection.

* * * * *